United States Patent
Ochel et al.

(10) Patent No.: US 10,322,223 B2
(45) Date of Patent: Jun. 18, 2019

(54) OXYGENATOR COMPRISING A HOLLOW-FIBER FILM BUNDLE

(71) Applicant: MEDOS Medizintechnik AG, Stolberg (DE)

(72) Inventors: Wolfgang Ochel, Massenbachhausen (DE); Andreas Maurer, Tuebingen (DE)

(73) Assignee: MEDOS Medizintechnik AG, Stolberg (DE)

( * ) Notice: Subject to any disclaimer, the term of this patent is extended or adjusted under 35 U.S.C. 154(b) by 170 days.

(21) Appl. No.: 15/117,308

(22) PCT Filed: Mar. 11, 2015

(86) PCT No.: PCT/DE2015/000110
§ 371 (c)(1),
(2) Date: Aug. 8, 2016

(87) PCT Pub. No.: WO2015/154736
PCT Pub. Date: Oct. 15, 2015

(65) Prior Publication Data
US 2016/0339164 A1 Nov. 24, 2016

(30) Foreign Application Priority Data
Apr. 11, 2014 (DE) .................. 10 2014 005 353

(51) Int. Cl.
*A61M 1/16* (2006.01)
*A61M 1/36* (2006.01)
(Continued)

(52) U.S. Cl.
CPC ........ *A61M 1/1698* (2013.01); *A61M 1/3638* (2014.02); *B01D 19/0031* (2013.01); *B01D 63/02* (2013.01); *B01D 2313/025* (2013.01)

(58) Field of Classification Search
CPC .............. A61M 1/1698; A61M 1/3627; A61M 1/3638; B01D 19/0031; B01D 63/02; B01D 2313/025
(Continued)

(56) References Cited

U.S. PATENT DOCUMENTS 5,817,279 A    10/1998  Eilers et al.
6,113,782 A *  9/2000  Leonard ............... B01D 63/022
                                                    210/321.89

(Continued)

FOREIGN PATENT DOCUMENTS

EP    0 765 683 A1    4/1997
EP    1 618 906 B1    1/2006
(Continued)

OTHER PUBLICATIONS

International Search Report of PCT/DE2015/000110, dated Jul. 8, 2015.
(Continued)

*Primary Examiner* — Philip R Wiest
(74) *Attorney, Agent, or Firm* — Collard & Roe, P.C.

(57) ABSTRACT

An oxygenator comprising a hollow-fibre film bundle is surrounded at least in certain areas by a bubble-retaining filter. In order to ensure an optimal function of the hollow-fibre film bundle and the bubble-retaining filter, it is proposed that a gas-permeable retaining structure is arranged between hollow-fibre film bundle and bubble-retaining filter.

11 Claims, 1 Drawing Sheet

(51) Int. Cl.
*B01D 63/02* (2006.01)
*B01D 19/00* (2006.01)

(58) Field of Classification Search
USPC .................................................. 422/44–48
See application file for complete search history.

(56) References Cited

U.S. PATENT DOCUMENTS

| | | | |
|---|---|---|---|
| 2007/0166190 A1* | 7/2007 | Ogihara | A61M 1/1698 422/45 |
| 2012/0277654 A1 | 11/2012 | Olson et al. | |
| 2014/0154137 A1* | 6/2014 | Kashefi Khorasani | A61M 1/1698 422/46 |

FOREIGN PATENT DOCUMENTS

| | | |
|---|---|---|
| EP | 1 839 691 B1 | 10/2007 |
| EP | 2 383 001 A1 | 11/2011 |
| JP | 2007-215992 A | 8/2007 |
| WO | 00/06357 A1 | 2/2000 |

OTHER PUBLICATIONS

Sueda et al, Development of an Outside Flow Membrane Oxygenator Using a Silicone Hollow Fiber, ASAIO Journal 1993, 4 pages.
English translation of International Preliminary Report on Patentability in PCT/DE2015/000110 dated Aug. 25, 2016.

* cited by examiner

OXYGENATOR COMPRISING A HOLLOW-FIBER FILM BUNDLE

CROSS REFERENCE TO RELATED APPLICATIONS

This application is the National Stage of PCT/DE2015/000110 filed on Mar. 11, 2015, which claims priority under 35 U.S.C. § 119 of German Application No. 10 2014 005 353.9 filed on Apr. 11, 2014, the disclosure of which is incorporated by reference. The international application under PCT article 21(2) was not published in English.

The invention relates to an oxygenator comprising a hollow-fibre film bundle which is surrounded at least in certain areas by a bubble-retaining filter.

Oxygenators are used for an exchange of gas between a blood stream and a gas stream. For this purpose oxygenators have hollow-fibre film bundles which form a transition membrane between gas stream and blood stream. Usually gas is guided inside the hollow fibres of the hollow-fibre membrane bundle whilst a blood stream is guided outside the hollow fibres. As a result, an exchange of gas is achieved between blood stream and gas stream at the hollow fibre membrane wall. Such an oxygenator is known, for example, from EP 765 683 to which reference is made in its full content.

If air bubbles are located inside the blood stream in the blood, these air bubbles are conveyed from the inlet of the oxygenator as far as the outlet. In order to retain such air bubbles, a filter element is proposed in EP 1 839 691 B1 which has a circumferential elasticity and rests against the hollow-fibre membrane bundle under tension. EP 1 618 906 B1 also describes such an oxygenator in which an inner circumferential surface of an annular bubble intercepting filter element is in contact with an outer circumferential surface of the annular hollow-fibre film bundle.

It has been found that the use of such a bubble-retaining filter negatively influences the function of the oxygenator.

It is therefore the object of the invention to further develop a generic oxygenator so that the bubble-retaining filter does not adversely influence the function of the oxygenator.

This object is solved with a generic oxygenator in which a gas-permeable retaining structure is disposed between hollow-fibre film bundle and bubble-retaining filter.

The gas-permeable retaining structure prevents such contact between bubble-retaining filter and hollow-fibre film bundle. The hollow fibres of the hollow-fibre film bundle can thus no longer lie directly on the filter openings of the bubble-retaining filter and it is thereby avoided that the function of the bubble-retaining filter is adversely affected by hollow fibres resting thereon. As a result of the gas-permeable retaining structure, the function of the hollow fibres on the outer side of the hollow-fibre film bundle is also no longer adversely affected by a bubble-retaining filter resting on the hollow fibre. The retaining structure therefore leads to the result that the complete functional capability of the bubble-retaining filter can be used and also the blood can flow around the radially outer hollow fibres.

The gas-permeable retaining structure also allows the blood to pass so that the blood which was initially guided along the hollow-fibre film bundle for an exchange of gas then flows firstly through the gas-permeable retaining structure and then through the bubble-retaining filter. The bubbles can thus be retained without adversely affecting the function of the oxygenator.

It is advantageous if the gas-permeable retaining structure rests against the hollow-fibre membrane bundle. Since the gas-permeable retaining structure prevents the bubble-retaining filter from resting on the hollow-fibre membrane bundle, the gas-permeable retaining structure can rest against the hollow-fibre film bundle. For this purpose, the gas-permeable retaining structure can be configured in such a manner that it does not adversely affect the function of the hollow-fibre film bundle.

In order to create an intermediate space between bubble-retaining filter and gas-permeable retaining structure, it is proposed that the retaining structure is flexible and exerts a compressive pressure on the hollow-fibre film bundle. Since the retaining structure need not have any defined pore diameter, it can be configured to be flexible and compress the hollow-fibre film bundle. The bubble-retaining filter on the other hand should not be stretched since the pore diameter is thereby enlarged with the result that the function of the bubble-retaining filter can be adversely affected.

In order to cooperate extensively with the hollow-fibre film bundle, it is proposed that the retaining structure surrounds the outer surface of the hollow-fibre film bundle. This outer surface is curved or extensively flat depending on the configuration of the oxygenator. In the case of stacked membranes the outer surface is usually extensively flat and in the case of wound oxygenators, the outer surface is usually curved or arranged radially to a central line.

One embodiment provides that the retaining structure is a network. Such a network can be produced with a defined pore diameter and it ensures a large free through area in relation to the required quantity of material.

Experiments have shown that it is advantageous if the retaining structure has a pore width of about 100 micrometers and preferably more than 100 micrometers. The bubble-retaining filter on the other hand should have a pore width of no more than 50 micrometres in order to function reliably.

It is advantageous if the bubble-retaining filter and the gas-permeable structure are each made from a woven fabric. Bubble-retaining filter and gas-permeable structure are preferably individual parts manufactured separately from each other which can each be manufactured as woven fabric from the same or different materials.

In one exemplary embodiment the bubble-retaining filter and the gas-permeable structure are made from the same material and preferably from a polymer, preferably a polyester (PET). In an alternative embodiment the gas-permeable retaining structure is made from a polymer, preferably from polyamide (PA).

An advantageous embodiment provides that the gas-permeable structure has a conical shape which corresponds to the shape of an inner wall of the oxygenator arranged radially outside the hollow-fibre film bundle. The conical shape of the gas-permeable structure allows the gas-permeable structure to be introduced into a conical inner wall of the oxygenator until it rests flat against the inner wall of the oxygenator. For this purpose it is advantageous if the gas-permeable structure has a certain intrinsic stability which allows the gas-permeable structure to be introduced into the space formed by the conical inner wall of the oxygenator so that it rests against the inner wall of the oxygenator during insertion.

It is particularly advantageous if the gas-permeable structure is pressed positively against an inner wall of a housing of the oxygenator arranged outside the hollow-fibre film bundle. This can be achieved by an elasticity of the gas-permeable structure which has the effect that the gas-permeable structure is pressed elastically against the inner wall. However, it can also be achieved whereby two conical vessel-like structures, as during the stacking of cups, are pressed into one another and thereby rest against one another.

An exemplary embodiment of an oxygenator is shown in the drawings and is described hereinafter.

In the figures

Figure 1:
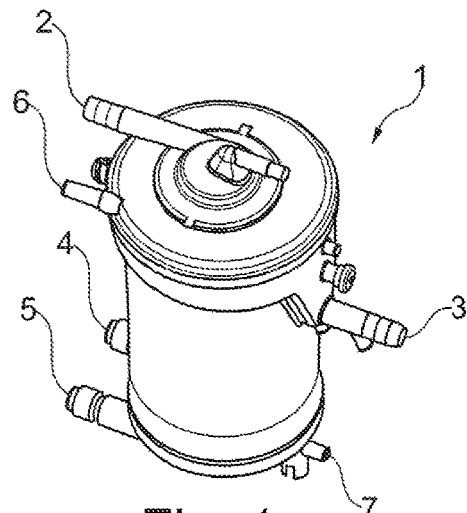
FIG. 1 shows a perspective view of an oxygenator.
Figure 2:
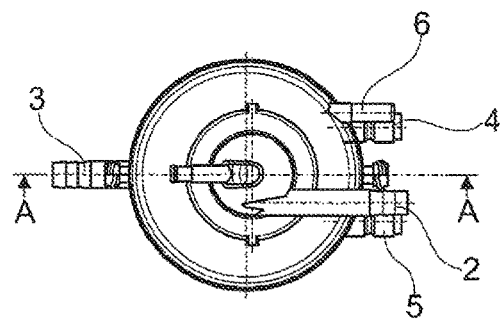
FIG. 2 shows a plan view of the oxygenator.
Figure 3:
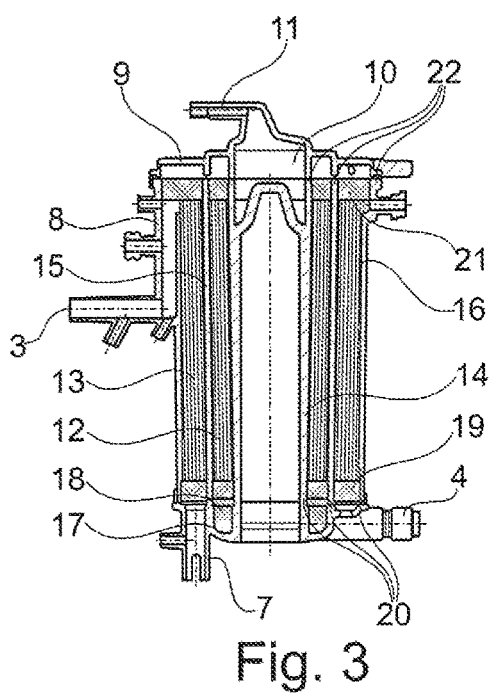
FIG. 3 shows a section through the oxygenator shown in FIG. 1.

The oxygenator 1 shown in FIG. 1 has a blood inlet 2 and a blood outlet 3. A water inlet 4 and a water outlet 5 are provided as further connections for temperature-control of the blood. Gas is supplied to the oxygenator at the inlet 6 and removed at the outlet 7.

The oxygenator housing 8 has a cover 9 via which the blood is supplied. If air bubbles should be located in the supplied blood, these are separated from the liquid by a forced blood vortex in the inlet region 10 and removed through the gas outlet 11.

The blood flows initially in the radially inner region along a hollow-fibre film bundle 12 in which water is guided for temperature control of the blood and then through a radially outer region in which a hollow-fibre membrane bundle 13 is arranged in order to achieve an exchange of gas between blood and gas flow through gas guided into the hollow fibres. Finally the blood leaves the oxygenator through the outlet 3.

The oxygenator housing has a radially inner wall 14, a middle wall 15 and an outer wall 16. The lower region of the oxygenator is formed by a base 17 in which water inlet and outlet 4, 5 and gas outlet 7 are located.

The hollow-fibre membrane bundles 12 and 13 are embedded in adhesive for sealing at the points 18 to 22.

Figure 4:
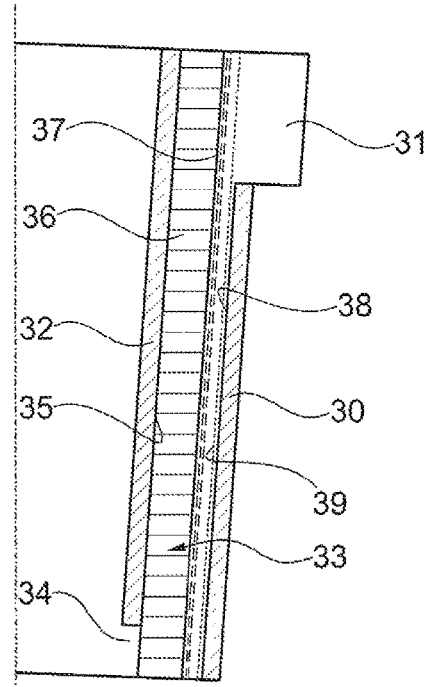
FIG. 4 shows schematically the cooperation of bubble-retaining filter and gas-permeable retaining structure.

FIG. 4 shows very schematically and only as an example an outer housing wall 30 with a blood outlet region 31 and an inner housing wall 32 located radially further inwards. Outer and inner housing wall are arranged slightly conically and concentrically to one another so that a space 33 lies between the housing walls which is radially delimited by walls arranged parallel to one another. Located in the lower region of the inner wall 32 is an inlet 34 which allows blood to flow from the inlet 34 through the space 33 to the outlet 31.

A hollow-fibre membrane bundle 36 is provided in the space 33 resting on the outer side 35 of the inner wall 32. This hollow-fibre membrane bundle 36 is pressed by a gas-permeable retaining structure 37 radially inwards onto the inner wall 32. The gas-permeable retaining structure thus acts as a hollow-fibre compression layer.

On the other side of the space 33 a bubble-retaining filter 39 rests against the inner side 38 of the outer wall 30 which must have flow passing through it at one point so that the blood can pass from the blood inlet 34 to the blood outlet 31.

In an oxygenator 1 as shown in FIG. 1, the opposite ends of the bubble-retaining filter 39 and the gas-permeable retaining structure 37 are embedded in adhesive at the points 18 to 22 like the hollow-fibre membrane bundle 12 and 13 and then cut off at the top and bottom side together with the overhanging adhesive.

In the installed state the gas-permeable retaining structure 37 is under tension in such a manner that it presses the hollow-fibre film bundle 36 against the inner wall 32. In so doing, the openings in the network-like retaining structure are held open by the tension so that a pore width is formed with a mean pore diameter of at least 100 micrometers.

The bubble-retaining filter 39 is located at a distance from the retaining structure 37, its pore width being designed so that the mean diameter of the pores is not more than 50 micrometers.

The invention claimed is:

1. An oxygenator comprising a hollow-fiber film bundle, which is surrounded by a bubble-retaining filter at least in certain areas,
    wherein a gas-permeable retaining structure is disposed between the hollow-fiber film bundle and the bubble-retaining filter, and
    wherein the retaining structure is flexible and exerts a compressive pressure on the hollow-fiber film bundle such that a channel is formed radially outside of the retaining structure.

2. The oxygenator according to claim 1, wherein the gas-permeable retaining structure rests against the hollow-fiber film bundle.

3. The oxygenator according to claim 1, wherein the retaining structure surrounds the outer surface of the hollow-fiber film bundle.

4. The oxygenator according to claim 1, wherein the retaining structure is a network.

5. The oxygenator according to claim 1, wherein the retaining structure has a pore width of more than 100 micrometers.

6. The oxygenator according to claim 1, wherein the bubble-retaining filter has a pore width of no more than 50 micrometers.

7. The oxygenator according to claim 1, wherein the bubble-retaining filter and gas-permeable retaining structure are each made from a woven fabric.

8. The oxygenator according to claim 1, wherein the bubble-retaining filter and gas-permeable retaining structure are made from the same material.

9. The oxygenator according to claim 1, wherein the gas-permeable retaining structure is made from a polymer.

10. The oxygenator according to claim 1, wherein the gas-permeable retaining structure has a conical shape which corresponds to the shape of an inner wall of the oxygenator located radially outside the hollow-fiber film bundle.

11. The oxygenator according to claim 1, wherein the gas-permeable retaining structure positively presses the hollow-fiber film bundle against an inner wall of a housing of the oxygenator.

* * * * *